United States Patent
Qing et al.

(10) Patent No.: US 7,672,493 B2
(45) Date of Patent: Mar. 2, 2010

(54) METHOD FOR ANALYZING MEDICAL IMAGE DATA USING LEVEL SET

(75) Inventors: Shuping Qing, Princeton, NJ (US); Hong Shen, Plainsboro, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1072 days.

(21) Appl. No.: 11/334,278

(22) Filed: Jan. 18, 2006

(65) Prior Publication Data

US 2006/0173272 A1 Aug. 3, 2006

Related U.S. Application Data

(60) Provisional application No. 60/648,565, filed on Jan. 31, 2005.

(51) Int. Cl.
*G06K 9/00* (2006.01)
*A61B 5/05* (2006.01)

(52) U.S. Cl. ................. 382/128; 600/407

(58) Field of Classification Search ......... 382/128–134, 382/103, 107, 164, 171, 173, 180, 181, 100, 382/203, 206, 217, 218, 228, 284; 378/2.4; 601/2–27; 600/407, 436–437; 128/920, 128/922–925; 345/417, 420; 358/515, 520, 358/530

See application file for complete search history.

(56) References Cited

U.S. PATENT DOCUMENTS

| | | | |
|---|---|---|---|
| 6,978,039 B2 * | 12/2005 | Cline et al. | 382/128 |
| 7,095,890 B2 * | 8/2006 | Paragios et al. | 382/173 |
| 7,424,153 B2 * | 9/2008 | Paragios et al. | 382/173 |
| 2004/0019267 A1 * | 1/2004 | Paragios et al. | 600/407 |
| 2006/0171576 A1 * | 8/2006 | Shen et al. | 382/128 |

\* cited by examiner

*Primary Examiner*—Samir A. Ahmed
*Assistant Examiner*—Mehdi Rashidian
(74) *Attorney, Agent, or Firm*—Donald B. Paschburg

(57) ABSTRACT

A method for analyzing medical image includes obtaining a plurality of surface fronts on an object, such points being disposed in a three dimensional volume in the object; varying the volume of each one of the points such volumes combining into a common volume; and terminating the process when the common volume reaches boundaries of the object.

5 Claims, 8 Drawing Sheets

Flowchart of rib segmentation refinement

Flowchart of rib segmentation refinement

Flowchart of the recursive tracing procedure.

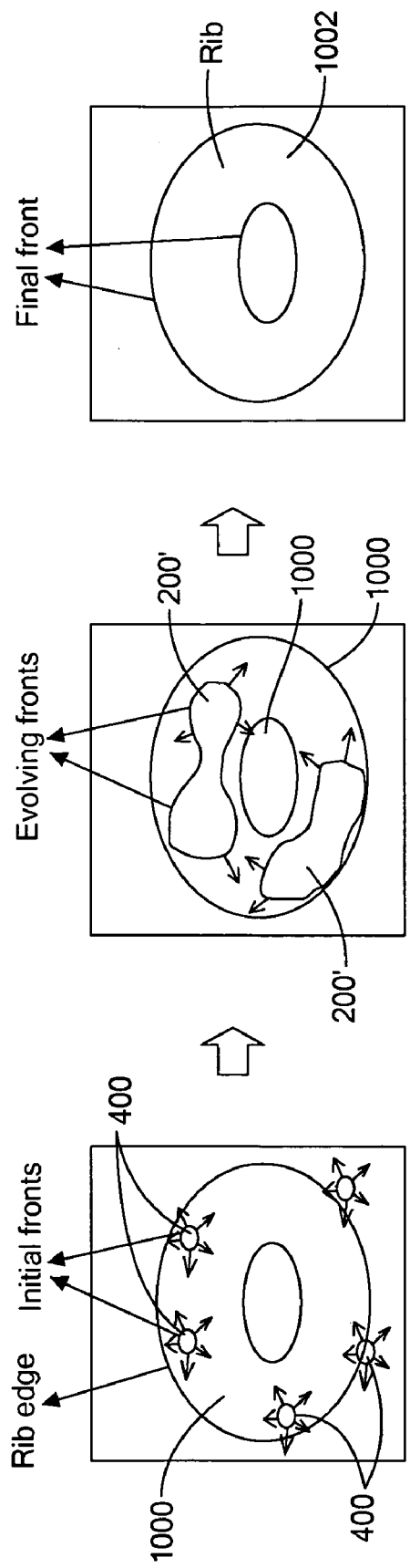
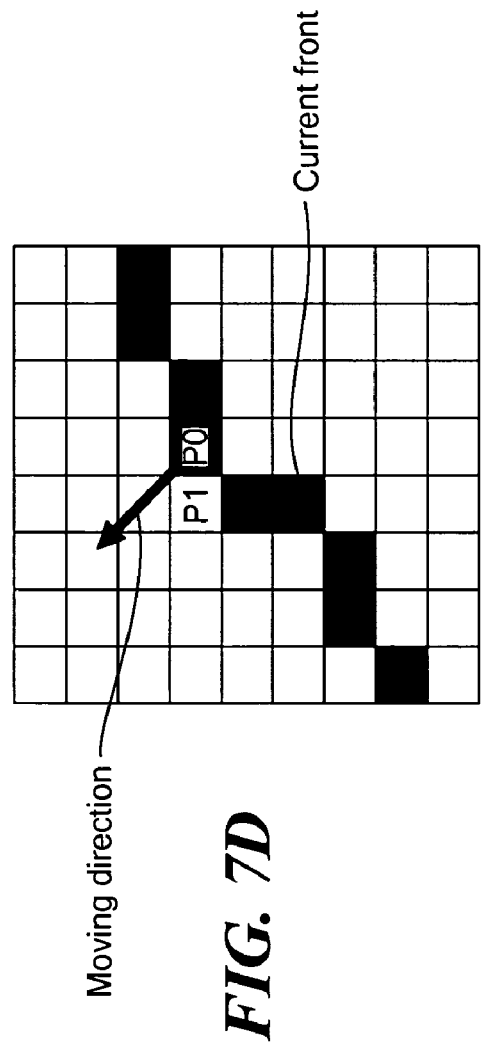
FIG. 7A
FIG. 7B
FIG. 7C
FIG. 7D

METHOD FOR ANALYZING MEDICAL IMAGE DATA USING LEVEL SET

CROSS-REFERENCED TO RELATED APPLICATIONS

This application claims priority from U.S. Provisional application Nos. 60/648,565, filed Jan. 31, 2005, which are incorporated herein by reference.

TECHNICAL FIELD

This invention relates generally to methods for analyzing medical image data and more particularly to methods for automatically providing reliable and precise segmentation of anatomical structures from volume data obtained with such system.

BACKGROUND

As is known in the art, medical image analysis plays an increasingly prominent role in Computer Aided Diagnosis (CAD) and therapy planning. As a preliminary stage of the analysis, segmentation of structures from medical images and reconstruction of these structures are difficult due to the large volume of the data involved and the complexity of the anatomic shapes of interest.

Three-dimensional (3D) visualization and labeling of rib structures, for example, in a CAD system provide important information for radiologists since they need to report any pathology pertaining to bones in a chest CT scan. The ribs have valuable properties common to bone tissues, i.e., they are rigid and stable in shape, and map to prominent intensities in CT data. Further, rib structures are highly ordered and symmetrical. Because of these features, rib feature group can be used for reliable registration and reference. To make full use of the structural advantages of the ribs, they should be extracted and labeled individually. There are 12 pairs of rib structures in a human body with 8-11 pairs visible in a chest CT volume dataset. They are connected at one end with the spine, and the upper pairs are also connected to the sternum.

SUMMARY

In accordance with the present invention, a method is provided for analyzing a medical image. The method includes obtaining a plurality of surface fronts on an object, such surface fronts being disposed in a three dimensional volume in the object; evolving each one of the surface fronts to form a common enclosed volume; and terminating the process when the common enclosed volume reaches boundaries of the object.

In one embodiment, the method includes: selecting medical imaging data representative of a plane traverse a region of an anatomical object or structure; obtaining data in a plane traverse the anatomical object; identifying a point disposed on the object; performing two-dimensional edge detection of the object to obtain contour points of the object in the plane comprising applying level set processing to the obtained contour points.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 7A-7D are sketches useful in understanding the invention.

Like reference symbols in the various drawings indicate like elements.

DETAILED DESCRIPTION

As will be described in more detail in connection with FIG. 1, the process includes: selecting medical imaging data representative of a plane traverse a region of an anatomical object or structure; obtaining data in a plane traverse the anatomical object; identifying a point disposed on the object; performing two-dimensional edge detection of the object to obtain contour points of the object in the plane comprising applying level set processing to the obtained contour points.

Subsequently, the process analyzes the obtained contour points in the plane to predict a point along a tracing direction for a subsequent plane, such tracing direction being along a length of the object and perpendicular to the tracing direction; and terminates when a predetermined criterion is satisfied, as described herein.

Figure 1:
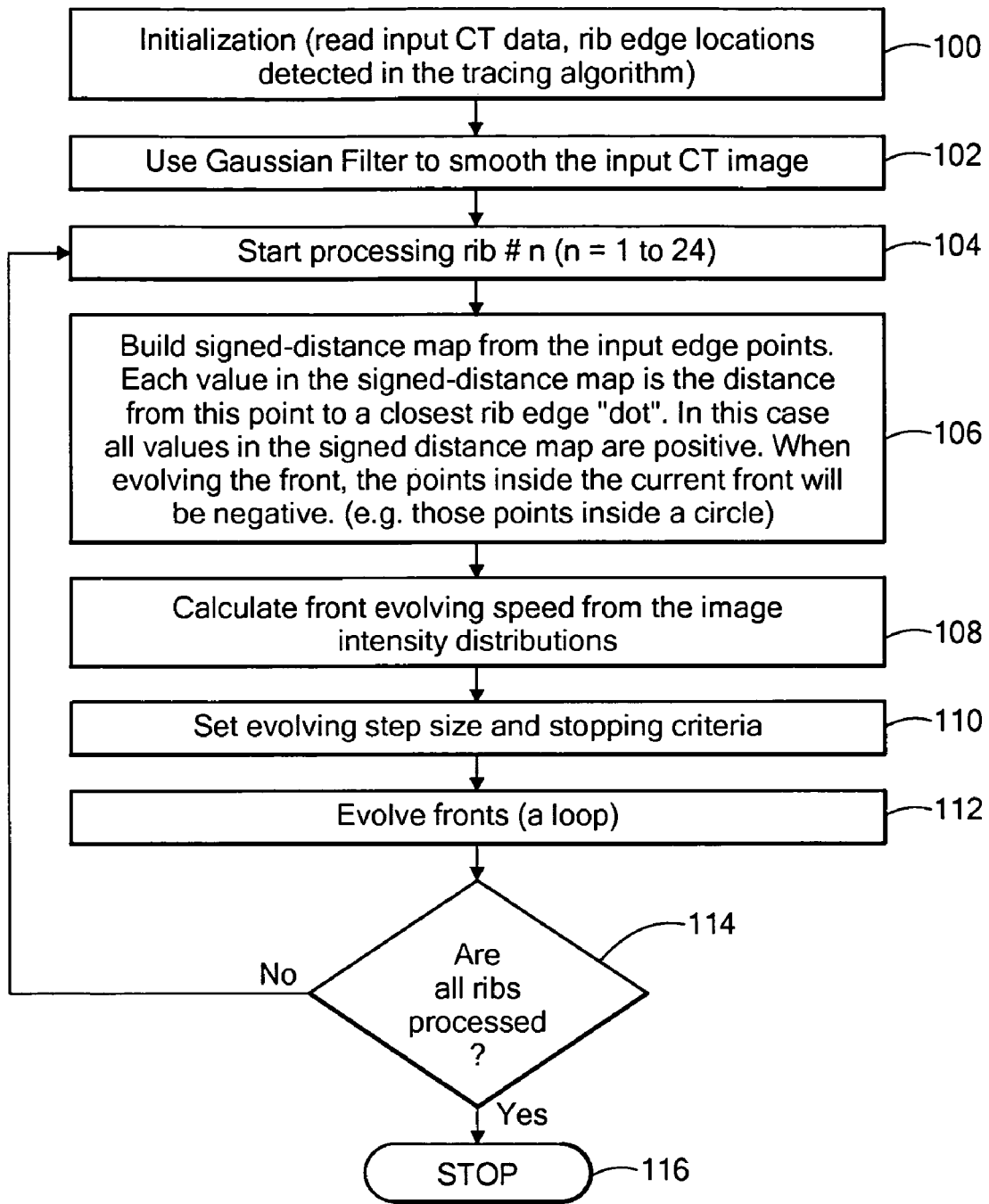
FIG. 1 is a flow diagram of the method according to the invention.

Thus, referring to in FIG. 1, in Step 100, the process initializes (i.e., read input CT data, rib edge locations detected in the tracing algorithm described herein. In step 102, the process uses Gaussian Filtering to smooth the input CT image. In Step 104, the process starts processing rib # n (n=1 to 24). In Step 106, the process builds a signed-distance map, described above, from the input edge points. Each value in the signed-distance map is the distance from this point to a closest rib edge point obtained in the first process. In this case all values in the signed distance map are positive. When evolving the front, the points inside the current front will be negative, (e.g., those points inside a circle). In Step 108, the process calculates front evolving speed from the image intensity distributions. In Step 110, the process sets evolving step size and stopping criteria. In Step 112, the process evolves fronts (a loop). In Step 114, the process determines whether all ribs are processed. If both, the process returns to Step 104; otherwise, the process stops, Step 616.

The level set method according to the present invention is selected as the core of the segmentation algorithm because its ability to handle topology changes naturally during deformation and it is represented implicitly as level sets of two-dimensional distance functions. Also, the implementation of the level set techniques is very straightforward.

The central idea behind the level set techniques is to represent the evolving surface as the zero-level set of a distance function. Let $\Gamma(t)$ be a closed surface propagating along its normal direction. Let $\Omega(t)$ be the region enclosed by $\Gamma(t)$ and $\phi(x(t), t)$ be the level set function where $x \in \Re^N$ such that:

$$\phi(x(t), t) = \begin{cases} D > 0 & \text{in } \Omega^c \\ 0 & \text{on } \Gamma \\ D < 0 & \text{in } \Omega \end{cases}$$

$\Gamma(t)$ is then represented as the zero level set of $\phi(x(t), t)$, i.e. $\phi(\Gamma(t), t) \equiv 0$.

By applying the chain rule we can further derive the level set equation given by S. Osher, and J. A. Sethian, in an article entitled "Fronts Propagating with Curvature-Dependent Speed: Algorithms Based on Hamilton-Jacobi Formulations", Journal of Computational Physics, 79, pp. 12-49, 1988] as:

$$\phi_t + F|\nabla \phi| = 0, \text{ given } \phi(x, t=0).$$

F represents the speed in the normal direction. This is the initial value formulation. The problem of evolving front $\Gamma(t)$ becomes solving the above equation. The speed term can be further represented in a general way as:

$$F = F_{prop} + F_{curv} + F_{adv}$$

where $F_{prop}$ is the propagation expansion speed, $F_{curv} = -\epsilon \kappa$ is the curvature controlled speed and $F_{adv}$ is the advection speed.

Based on the type of propagation force, the level set techniques are classified into three groups: 1) the propagation force is constant. 2) The propagation force is determined by statistical means and 3) a set of seeds deform under the influence of image information; as described by J. S. Suri, S. Singh, S. Laxminarayan, X. Zeng, K. Liu and L. Reden, on an article entitled "Shape Recovery Algorithms Using Level Sets in 2-D/3-D Medical Imagery: A State-of-the-Art Review". Our algorithm is based on the first type of level set techniques and we chose the Chan-Vese model [T. F. Chan and L. A. Vese, "Active Contours without edges", IEEE transactions on Image Processing, 2001, 10(2): 266-277] because it is region-based and independent of edge information.

Mathematical Descriptions (a) Mathematical Model

Our choice of a mathematical model for the surface evolving comes from the following facts. 1) The ultimate goal is to extract individual rib surface. 2) Cortical bones (exterior layer of rib) have much higher intensity then surrounding tissues and vessels. While trabecular bones have lower intensity and therefore form a dark region inside each rib. A region growing method fails to segment the ribs as explained previously, we choose a region-based level set method to overcome the difficulties introduced by the complexity of the local structure and the fact that no clear-cut threshold exists between bone structure and other tissues.

The energy functional of the Chan-Vese model is defined by:

$$F(C, c_1, c_2) = \mu \cdot (\text{length}(C))^p + \nu \cdot \text{area(inside } C) + \lambda_1 \int_{insideC} |\mu_0 - c_1|^2 dx + \lambda_2 \int_{outsideC} |\mu_0 - c_2|^2 dx$$

where $c_1$ and $c_2$ are average intensities inside and outside C respectively. If we replace C with $\phi$ the minimization problem becomes:

$$\inf_{\phi, c1, c2} F(\phi, c_1, c_2)$$

The corresponding gradient flow for $\phi$ is:

$$\frac{\partial \phi}{\partial t} = \delta_\varepsilon(\phi)\left[\mu p \left(\int_\Omega \delta_\varepsilon(\phi)|\nabla \phi|\right)^{p-1} \kappa - \lambda_1(\mu_0 - c_1)^2 + \lambda_2(\mu_0 - c_2)^2\right]$$

let $\lambda_1 = 1, \lambda_2 = 1, p = 2$ $$\frac{\partial \phi}{\partial t} = \delta_\varepsilon(\phi)\left[\mu \left(\int_\Omega \delta_\varepsilon(\phi)|\nabla \phi|\right) \kappa - (c_2 - c_1)\left(\mu_0 - \frac{c_2 + c_1}{2}\right)\right]$$

In our implementation, the curvature $\kappa$ is approximated by the central difference approximation.

(b) Signed Distance Function:

The signed distance function satisfies the Eikonal equation $|\nabla T| = 1$. We use fast sweeping algorithm [H. Zhao, S. Osher, B. Merriman and M. Kang, "Implicit and Non-parametric Shape Reconstruction from Unorganized Data Using a Variational Level Set Method", Computer Vision and Image Understanding. Vol. 80, 2000, pp 295-319. to solve this function. First, fix the distance values at all given input points, i.e. initial fronts. Then for each grid point (i, j, k) whose distance is not known apply the following monotone upwind discretization:

$$[(d_{i,j,k} - x_{min})^+]^2 + [(d_{i,j,k} - y_{min})^+]^2 + [(d_{i,j,k} - z_{min})^+]^2 = h^2$$

where h is the grid size and $$(D)^+ = \begin{cases} D & D > 0 \\ 0 & D \leq 0 \end{cases}, x_{min} = \min(d_{i-1,j,k}, d_{i+1,j,k}),$$

$y_{min} = \min(d_{i,j-1,k}, d_{i,j+1,k})$, $z_{min} = \min(d_{i,j,k-1}, d_{i,j,k+1})$. According to [ ], a unique solution exists for this equation.

(c) Re-Initialization:

Ideally, at some point in time the level set function needs to be rebuilt based on the signed distance function. In our algorithm, the fast sweeping algorithm is used to re-compute the signed distance function by solving the Eikonal equation: $|\nabla T| = 1$. Then the new signed distance function is simply substituted for the level set function. The re-initialization is performed for every 20 iterations.

Results from Two Types of Initial Surface Fronts

The result of front evolvement in level set methods heavily depends on initial front. As discussed above, there are boundaries between the cortical bone and the trabecular bone inside the rib structure. Depending on whether one wants to extract the internal or external surface, different initial front designs are used. A properly selected initial front prevents surfaces from evolving into neighboring bone structures. Moreover, a close initial front will reduce the time for the PDE (partial differential equation) to converge and hence the computation cost.

Figure 2:
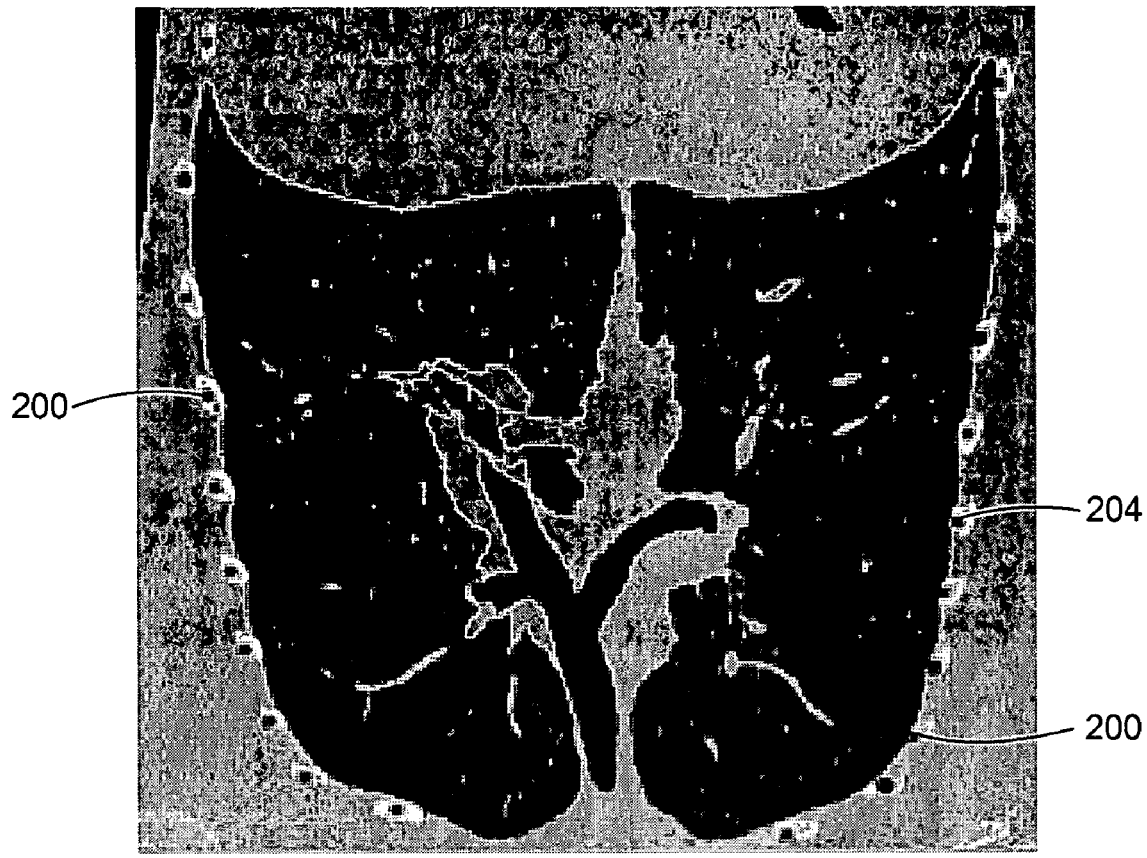
FIG. 2 is a 2D image extracted at a middle Coronal plane within a volume data being processed in accordance with the method of FIG. 1A.
Figure 2:
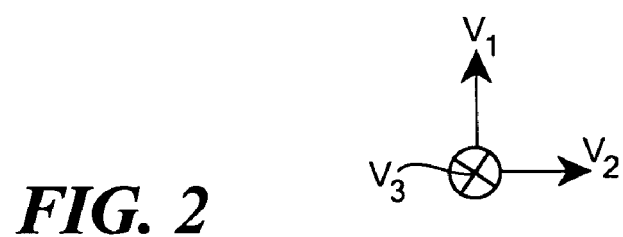

The input data for this level set algorithm uses either: (1) data from the surface reconstructed from the sample boundary points, as shown in FIG. 2; or (2) the directly using the sample boundary points described herein.

Figure 1A:
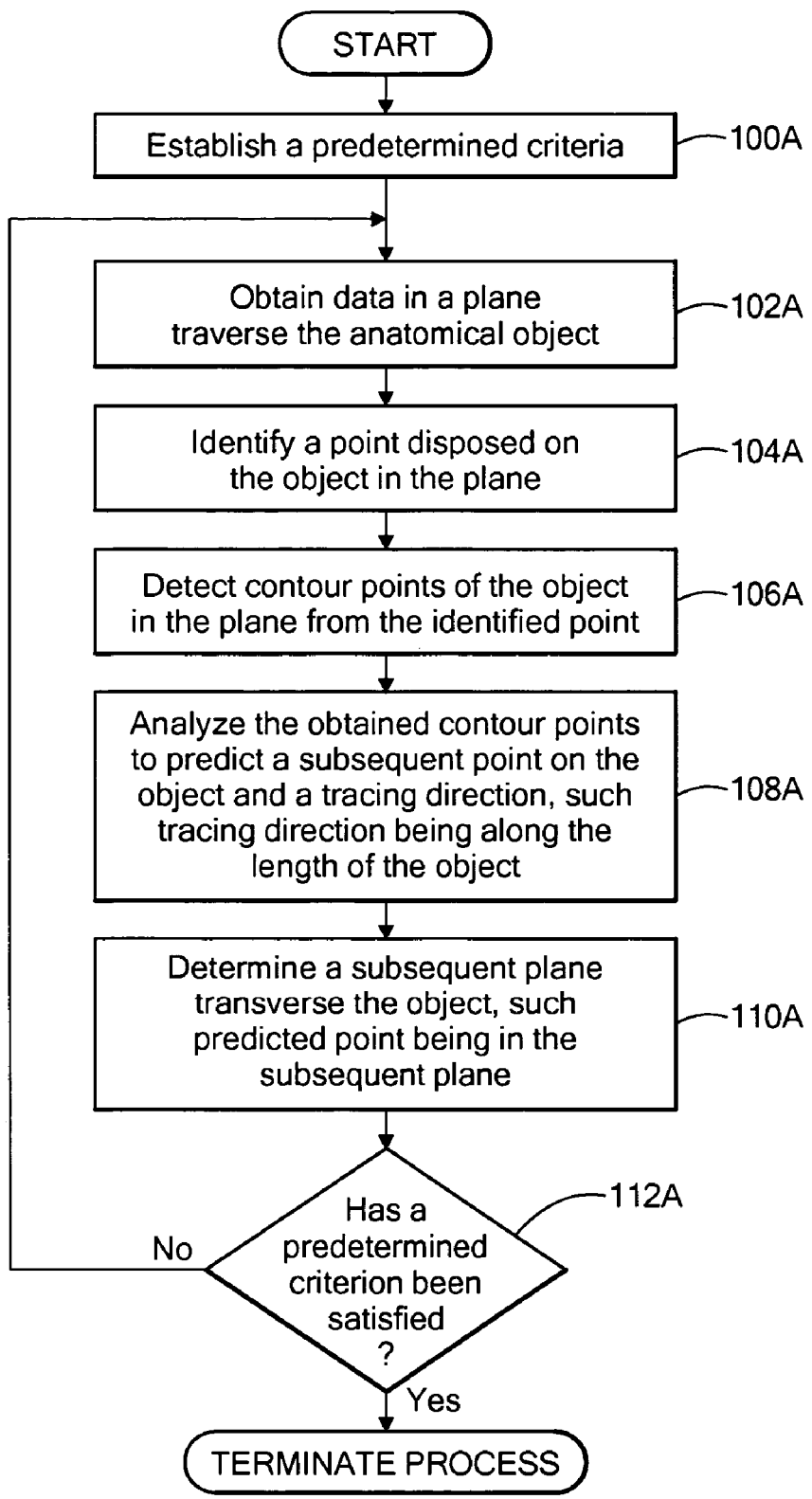
FIG. 1A is a flow diagram of the method for use in the method according to the invention.

More particularly, when using the sample boundary points described herein and referring to FIG. 1A, the process establishes a predetermined criteria, Step 100A; obtains data in a plane traverse the anatomical object, Step 102A; identifies a point disposed on the object in the plane, Step 104A; detects contour points of the object in the plane from the identified point, Step 106A; analyzes the obtained contour points to predict a subsequent point on the object and a tracing direction, Step 108A, such tracing direction being along the length of the object; determines a subsequent plane transverse the object, such predicted point being in the subsequent plane, Step 110A; repeats the process until the predetermined criterion is satisfied, Step 112A.

More particularly, the method establishes a predetermined criteria; obtains data in a plane traverse each one of a plurality of the anatomical objects, such as ribs in a rib cage; identifies a point disposed on a corresponding one of the plurality of objects, i.e., here one of the ribs, in the plane; detects contour points of each one of the objects in the plane from the identified points; analyzes the obtained contour points to predict a subsequent point on the object, here the one rib, and a tracing direction, such tracing direction being along the length of a corresponding one of the objects; determines subsequent planes, each one of the subsequent planes being transverse a corresponding one of the objects, such predicted points being in the subsequent planes; repeats the process until the predetermined criterion is satisfied.

In this example, the method obtains data in a plane traverse each one of a plurality of the anatomical objects, such as ribs terminating in a common support, here for example a vertebra attached to the ribs; identifies a point disposed on a corresponding one of the plurality of objects in the plane; detects contour points of each one of the objects in the plane from the identified points; analyzes the obtained contour points to predict a subsequent point on the object and a tracing direction, such tracing direction being along the length of a corresponding one of the objects; determines subsequent planes each one of the subsequent planes being transverse a corresponding one of the objects, such predicted points being in the subsequent planes; repeats the process until the tracing direction reaches the common support.

More particularly, the process in this example, extracts around 20 contour points at each tracing step, (i.e., in each cross-section) along the tracing direction, which represent the local contour and outer surface shape of the object, here the rib. The sample points at all steps form the global contour and outer surface. Based on these sample points, the rib outer surface can be obtained using a surface reconstruction algorithm. Reference is made to a paper by H. Shen and L. Liang, M. Shao and S. Qing entitled "Tracing Based Segmentation for the Labeling of Individual Rib Structures in Chest CT Volume Data", International Conference on Medical Image Computing and Computer-Assisted Intervention (MICCAI) 2004, the subject matter thereof being incorporated herein by reference.

More particularly, seed points 200A are detected from a 2D image that is extracted at a middle sagittal plane within the volume data, as shown in FIG. 2A. On this sagittal image, each rib 202A has a cross-section shown as a hollow-bright, i.e., high intensity, region, 204A. By shape analysis, the process detects the center of these regions 204 and uses them as the seed points 200A; one seed point 200A for each rib 202A. The tracing starts from seed points 200 disposed at in a selected plane along the tracing direction, v3, here along the length of the rib, such length projecting into the plane and proceeds successively along the direction of v3 and along its opposite direction to thereby process data obtained along the entire length of the rib. Edges or boundaries of the rib in each plane are detected by detecting intensity changes.

Model, Assumptions and Basic Methods

Figure 3A:
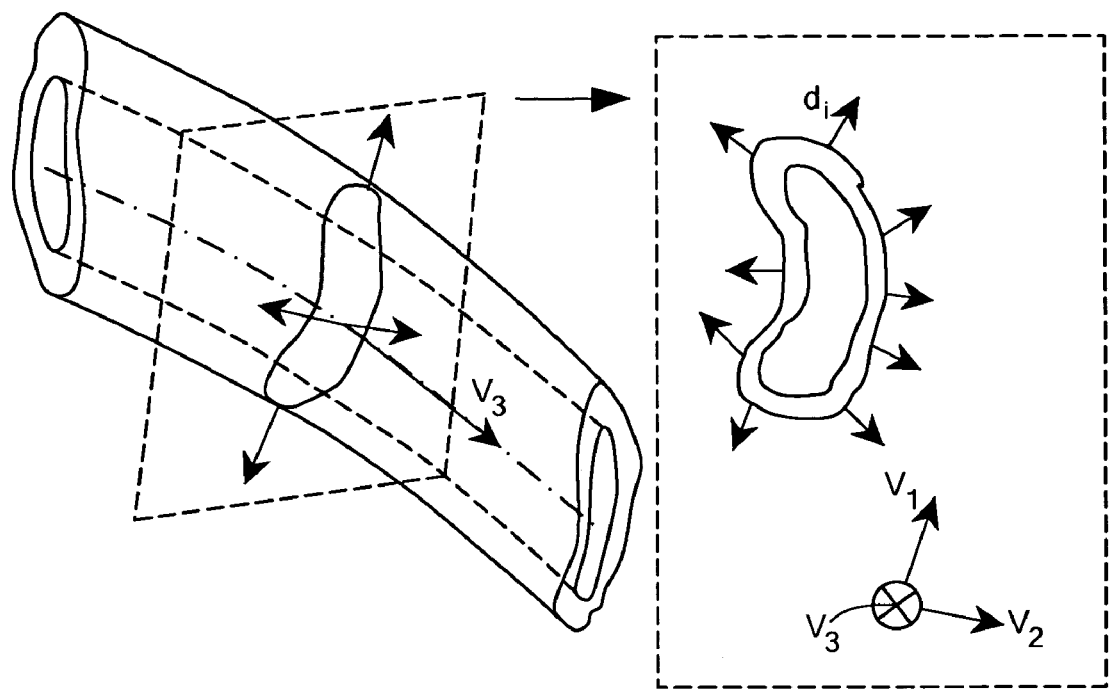
FIGS. 3A-3B are geometric models of an anatomical structure, here a rib structure, being analyzed in accordance with the method of FIG. 1A.
Figure 3B:
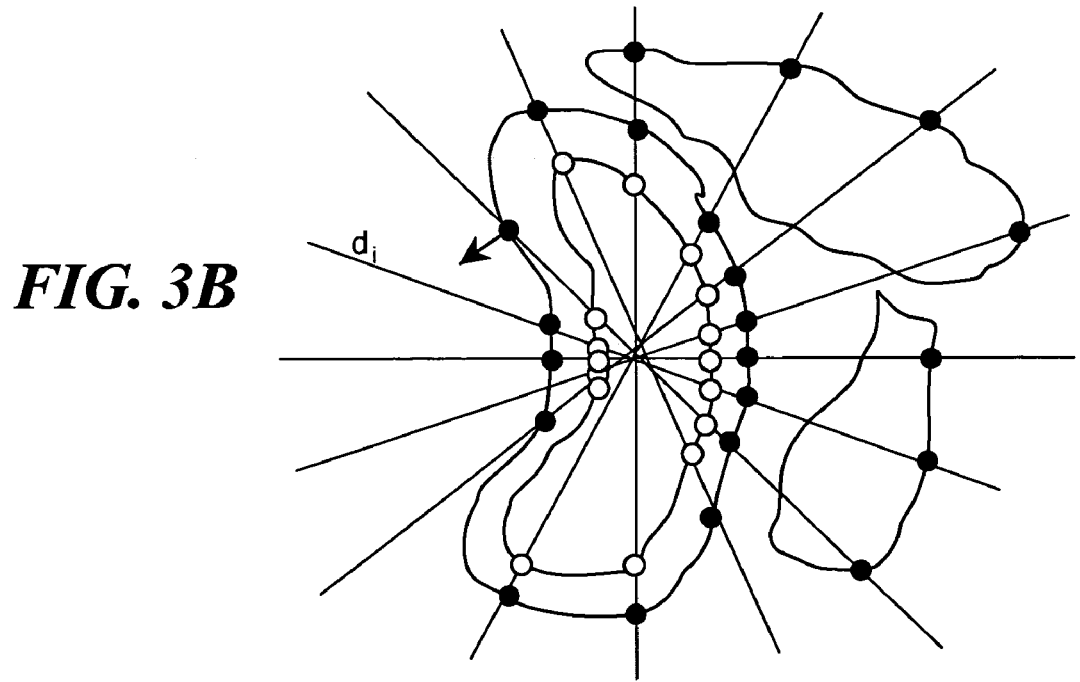

Referring now to FIGS. 3A and 3B shows the geometric model of a rib structure is shown. We assume the normals of the outer surface are perpendicular to the centerline direction (noted as $v_3$) everywhere. At each tracing step, the contour of the rib is extracted in the cross-section plane with normal $v_3$. Referring to FIG. 3B, at each step, all candidate edges are detected in each searching direction. The inner edges are removed. An individual rib can be modeled as a tube-like structure, which is elongated, curved and internally hollow, as shown in FIG. 3A. The cross-sections of a rib vary both in shape and size.

In our model, we assume that the outer surface is smooth everywhere, and more importantly, the surface normals $d_i$, i=1 . . . n are roughly perpendicular to the centerline direction. This leads to our basic method of computing the tracing direction given the surface normals of detected edge points. Suppose the unit gradient vectors of n edge points on a local cross-section represent the local surface normals, and we compute a covariance matrix of all unit vectors $d_i$, $$C = \sum_{i=1}^{n} (d_i - \bar{d})^t (d_i - \bar{d}), \quad (1)$$

where $\bar{d}$ is average of all edge gradients. We compute the eigenvalues $\lambda_1 \geq \lambda_2 \geq \lambda_3$, with corresponding eigenvectors $v_1$, $v_2$, and $v_3$. Since $v_3$ is the new basis direction where the gradient vectors vary the least, it is perpendicular to the 2D subspace of the unit vectors. Therefore we take this vector as the centerline direction estimated from the gradient of local edges. The recursive tracing can then be described as $$p^{(i+1)} = p^{(i)} + \alpha v_3 \quad (2)$$

in which the current centerline point $p^{(i+1)}$ is determined from the previous centerline point $p^{(i)}$, and $\alpha$ is the step size.

At each step, we define a cross-section plane whose normal is the previous centerline direction. As shown in FIG. 3A, the intersection points of this plane and the rib outer surface form a rib contour, which are extracted using 3D edge detection. However, we do not perform edge detection on each pixel on the plane. Rather, as shown in FIG. 3B, we extend 20 equal spaced search directions from the initial point $p^{(i)}$ to look for strong edges. In many cases, more than one edge points are detected along each search direction.

Figure 4:
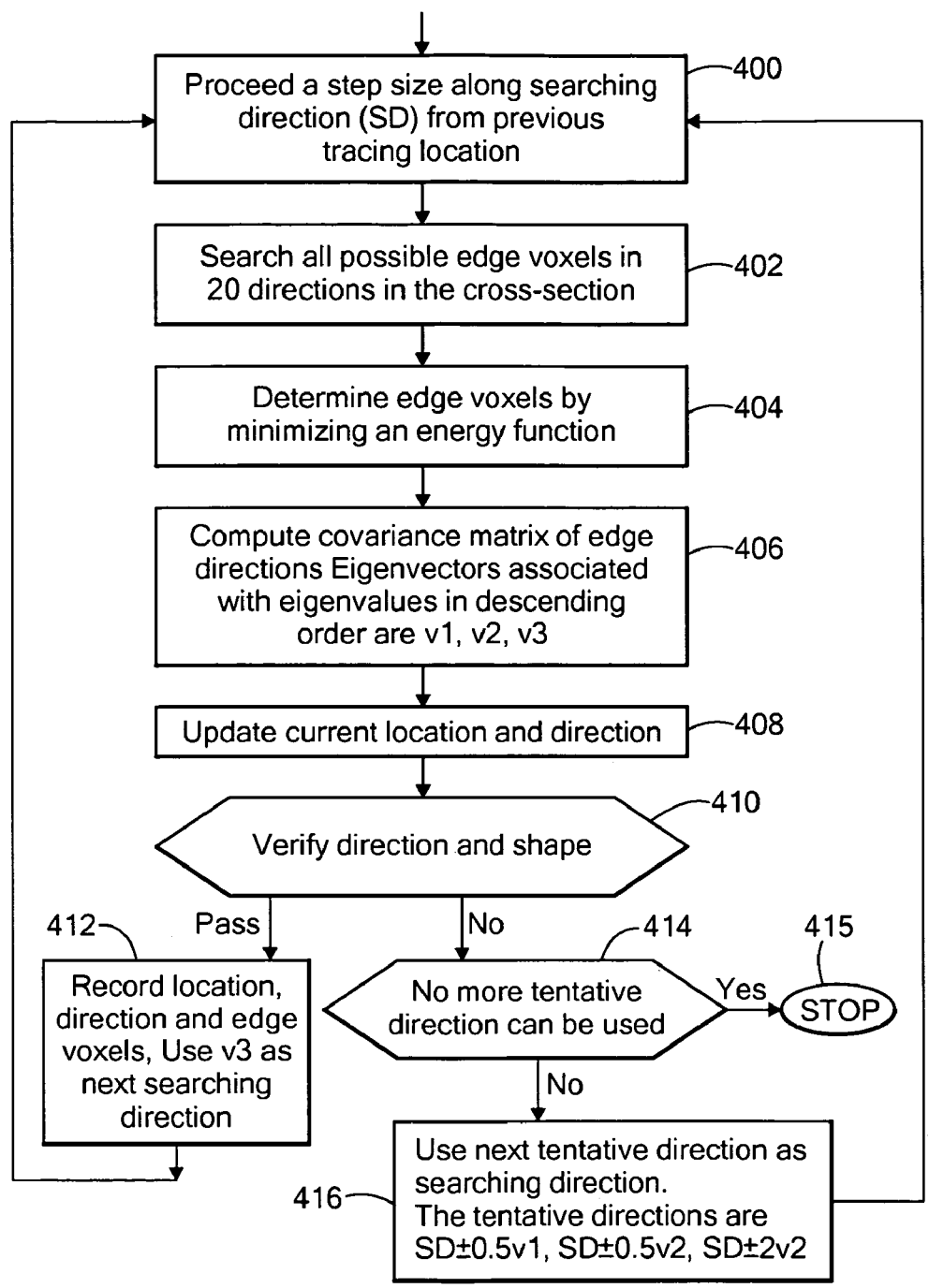
FIG. 4 is a more detailed flow diagram of a method of FIG. 1A.

A recursive tracing procedure used after seed point detection is described in the flow chart of FIG. 4. The process is a loop, where, in Step 400, provides a step size along a searching direction (SD) from a previous tracing location. In Step 402, the process searches all-possible edge voxels in here 20 directions in the cross section. In Step 404, the process determines edge voxels by minimizing an energy function. The energy function consists of two terms. The first term measures the total length of the edge contour and the second terms measures curvature. It is represented as:

$$E = \sum_{i} (E_d(i) + \alpha E_c(i))$$

where α is a weight that balances two energy terms.

In Step 406, the process computes the covariant matrix of edge directions. Eigenvectors associated with eigenvalues in depending order are v1, v2, v3, where v1 and v2 are orthogonal to the tracking direction v3.

In Step 407m the process updates the current location and direction.

In Step 410, the process verifies the direction and shape.

If in Step 410 the direction and shape are verified, the process, in Step 412, the process records the location, direction and edge voxels for use by, for example, a level set refinement process described herein. Also, the process uses v3 as the next searching direction and returns to Step 400 to perform the search in such next searching direction.

On the other hand, if in Step 410, the direction and shape are not verified, the process determines in Step 414 whether any more directions can be used. If not, the process stops, Step 514. The stopping criterion are: whether the correlation between SD and predicated direction is greater than a first predetermine correction threshold, corr1_thresh; whether the correlation between searching direction (SD) and the searching direction of the previous step (NSD) is greater than a second predetermined threshold, d corr2_thresh1; and whether the number of valid edge voxels is greater than a predetermined value, here for example 10.

If there are other directions, the process, in Step 416, uses the next tentative direction as a search direction. The tentative directions are SD±0.5v1, SD±0.5v2, and SD±0.5v3.

More particularly, on each tracing step, the process first finds the edge locations of the rib cross-section in 20 directions within the plane of the cross-section, Step 402. Afterwards, the process computes, in Step 406, the covariance matrix of the edge directions. The local rib direction is computed as the eigenvector associated with the smallest eigenvalue of the covariance matrix. In this way, the tracing direction makes the largest angles with the local edge directions, and therefore is approximately parallel to the rib centerline. This direction will be used to determine the next tracing location by jumping a number of voxels in that direction.

Correct searching directions rely on the accurate positions and directions of rib edge voxels. This tracing algorithm incorporates some considerations to improve the accuracy of the locations and directions of rib edge voxels, while keeps computational cost at lower level. Tracing stops when a certain set of stopping criterions is met.

More particularly, the process for detecting the centerline point includes:

Special Edge Detection

The process does not perform edge detection on every voxel on the cross-section, but only find the edge voxels in 20 directions from the center location, as described in Step 402. Instead of simple 3D edge detector, a more sophisticated and more accurate edge detector is used. The detector is based on fitting a polynomial function to the image intensity in a small neighborhood and computing the analytical gradient value associated with this function. Experiments show that this edge detector is much more effective for finding rib edges, while the result total processing time of tracing is only several seconds more than the Prewitt edge operator.

Jointly Determination of Edge Voxels by Dynamic Programming

For each of the 20 directions, the process, in Step 04, determines several (2~3) voxels that meet the edge criteria. The process computes an energy function from all the candidate edge voxels in the 20 directions. The true edge voxels in all directions are jointly determined when the energy is minimized. The process uses the dynamic programming technique to search for the minimum energy. Using this method rather than looking for maximum gradient magnitude, the process is able to avoid distractions from other nearby bone structures.

Retrospective Tracing

When stopping criterion is met, Step 415, the process goes back to previous valid tracing location, and adjust the searching direction, Step 400. There will be several such attempts before the tracing stops. This retrospective strategy makes the algorithm more robust.

Both Rib Centerlines and Contours are Extracted at the Same Time

The process records in Step 412, rib centerline and edge voxels at each step. The 20 edge voxels in the selected directions, which represents a sampling of local shape, forms the contour of the cross-section. All cross-section contours along the rib form the rib outer surface.

(1) Exterior Rib Surface Searching Staring from Initially Constructed Surface

Here, the level set process uses the one surface reconstructed from the traced boundary points. The rib volume is first reconstructed using the Delauney 3D triangulation algorithm described by Brian Lee Curless, Ph.D thesis "New Methods for surface reconstruction from range images", 1997.

Afterwards, the surfaces are extracted from the binary volume. Shown in FIG. 2 are the zero level set points 200 on one slice, i.e., plane. From FIG. 2, it is noted that the front is quite close to the outer rib boundary. On the other hand, surfaces are very bumpy, and at many places the surface does not reflect the actual rib shape. The propagation force of the level set functional will force the front to move close to the real rib edges while the curvature-dependent speed term will provide smoothness as will be described in connection with FIGS. 7A-7D.

Figure 5:
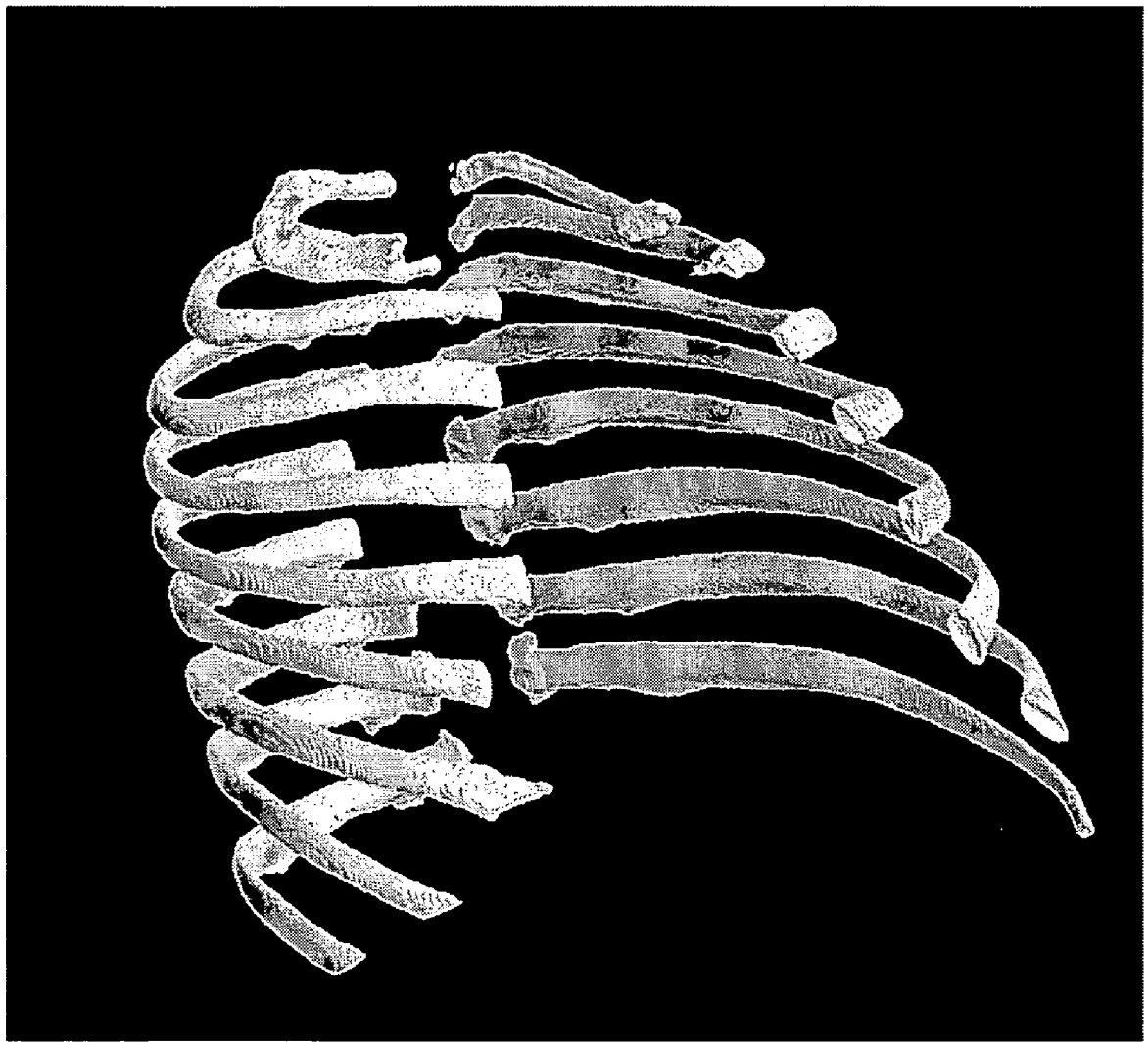
FIG. 5 is an image of rib surfaces obtained with the process of FIG. 1A.
Figure 6:
FIG. 6 is an axial slice image shows after 60 iterations of the method of FIG. 1.

After 60 iterations, the fronts reach the rib edges and sharp corners are recovered during the propagation. A 3D visualization is shown in FIG. 5. As shown in FIG. 5, the final surfaces are smooth and fit where to the rib outer boundaries. It can also be seen that at convergence the final fronts are the exterior rib edges. This method is suitable for whole rib segmentation and rib surface reconstruction. This is because that the original surface is close to the outer boundary, and therefore will not be attracted to the inner structure boundaries. An axial slice of the result is shown in FIG. 6.

(2) Segmentation of Both Interior and Exterior Structures Starting from Sample Points 300

In this approach, the propagation starts from the initial front that is composed of multiple mini-spheres, each center at one sample boundary point 200 from the tracing result. The fronts are allowed to evolve freely until they hit rib edges. Because of the ability of the level set method to capture the topology changes, the evolving fronts will eventually merge together and form the rib surfaces. We demonstrate this process with the drawings shown in FIGS. 7A-7C. From the pictures we can see how the zero level set evolves at different stages.

More particularly, in FIG. 7A the points 200 are shown in the positions obtained from the process described above in connection with FIG. 1. Note that the actual rib boundaries are shown by the dotted outline 1000. The points 200 are then expanded and combined to regions 200' as shown in FIG. 7B by the level set process described above and in the flow diagram of FIG. 1. The regions 200' converge as shown in FIG. 7C. At convergence, the zero level set reflects the edge or boundary of the rib 1002.

Thus, referring to FIGS. 7A-7D, the evolving of the fronts (3D surfaces) using level set method may be summarized as follows:

The fronts are actually the current segmentation boundaries. The fronts are moving in the direction as shown in the FIG. 7D. For each point of the front curve (surface in 3D), the front moves to its neighboring point (for example from p0 to p1) based on two criteria: (1) intensity; and (2) curve (surface) smoothness. The criterion of intensity guarantees the inside and outside portions of the front will finally reach to the state such that the image is well segmented into foreground and background. The second criterion guarantees the final front will be smooth enough.

The result shows that the level set method naturally conforms to local structures if the initial fronts are of a free format. Therefore it can detect the interior edges of the ribs, and the trabecular bones are differentiated from cortical bones in the segmentation results. The extracted inner surface is of particular importance since only the outer surface is detected using the first approach. To obtain a good result, all initial points need to be located inside or close to the rib structure. An initial point on a neighboring bone will result in the fronts evolving into these bones. On the other hand, the first approach has the ability of constraining the surface evolving more strictly since the initial front is one surface rather than many mini-spheres.

Thus, the method obtains a plurality of points on an object, such points being disposed in a three dimensional volume in the object; varying the volume of each one of the points such volumes combining into a common volume; and terminating the process when the common volume reaches boundaries of the object.

As described above, the process uses a region-based level set approach to refine rib segmentation result. The input to this algorithm can be either sample points on or close to rib edges or initial rib surfaces. The result can be used in rib labeling or 3D visualization in a diagnosis system.

A number of embodiments of the invention have been described. Nevertheless, it will be understood that various modifications may be made without departing from the spirit and scope of the invention. For example, it should be noted that the method works well with high resolution and relatively low resolution CT images and can be extended to other modalities such as MR. Accordingly, other embodiments are within the scope of the following claims.

What is claimed is:

1. A method for analyzing a medical image generated from data obtained from medical imaging equipment, comprising: using medical imaging apparatus to perform the steps of:
    obtaining from the data a plurality of surface fronts on an image of an object obtained from the data, such surface fronts being disposed in a three dimensional volume in the object;
    evolving each one of the surface fronts to form a common enclosed volume; and
    terminating the process when the common enclosed volume reaches boundaries of the object and;
    wherein the obtaining step comprises:
        (a) obtaining the data in a plane traverse an anatomical object;
        (b) identifying a point disposed on the object in the plane;
        (c) detecting contour points of the object in the plane from the identified point;
        (d) analyzing the obtained contour points to predict a subsequent point on the object and a tracing direction, such tracing direction being along the length of the object; and
        (e) determining a subsequent plane transverse the object, such predicted point being in the subsequent plane; establishing a predetermined criteria; and repeating (a) through (e) the process until the predetermined criterion is satisfied.

2. A method for analyzing a medical image generated from data obtained from medical imaging equipment, comprising: using medical imaging apparatus to perform the steps of:
    obtaining from the data a plurality of surface fronts on an image of an object obtained from the data, such surface fronts being disposed in a three dimensional volume in the object;
    evolving each one of the surface fronts to form a common enclosed volume;
    terminating the process when the common enclosed volume reaches boundaries of the object and
    wherein the obtaining step comprises:
        (a) obtaining the data in a plane traverse each one of a plurality of an anatomical objects;
        (b) identifying a point disposed on a corresponding one of the plurality of objects in the plane;
        (c) detecting contour points of each one of the objects in the plane from the identified points;
        (d) analyzing the obtained contour points to predict a subsequent point on the object and a tracing direction, such tracing direction being along the length of a corresponding one of the objects; and
        (e) determining subsequent planes each one of the subsequent planes being transverse a corresponding one of the objects, such predicted points being in the subsequent planes; establishing a predetermined criteria; and repeating (a) through (e) the process until the predetermined criterion is satisfied.

3. A method for analyzing a medical image generated from data obtained from medical imaging equipment, comprising: using medical imaging apparatus to perform the steps of:
    obtaining from the data a plurality of surface fronts on an image of an object obtained from the data, such surface fronts being disposed in a three dimensional volume in the object;
    evolving each one of the surface fronts to form a common enclosed volume;
    terminating the process when the common enclosed volume reaches boundaries of the object and
    wherein the obtaining step comprises:
        obtaining data in a plane traverse each one of a plurality of an anatomical objects terminating in a common support;
        identifying a point disposed on a corresponding one of the plurality of objects in the plane;
        detecting contour points of each one of the objects in the plane from the identified points;
        analyzing the obtained contour points to predict a subsequent point on the object and a tracing direction, such tracing direction being along the length of a corresponding one of the objects;
        determining subsequent planes, each one of the subsequent planes being transverse a corresponding one of the objects, such predicted points being in the subsequent planes; repeating the process until the tracing direction reaches the common support.

4. The method recited in claim 1 wherein the objects are ribs of an anatomical body and wherein the common support is a vertebra attached to the ribs.

5. A method for analyzing a medical image generated from data obtained of a tubular structure, comprising:

using medical imaging apparatus to perform the steps of:

obtaining from the data a plurality of surface fronts on an image of an object obtained from the data, such surface fronts being disposed in a three dimensional volume in the object;

evolving each one of the surface fronts to form a common enclosed volume;

terminating the process when the common enclosed volume reaches boundaries of the object and wherein the obtaining step comprises:

(a) selecting medical imaging data representative of a plane traverse a region of the tubular structure;

(b) defining a mathematical model of the tubular structure from the data;

(c) identifying from the model a seed point disposed in a central region of the tubular structure and in the plane;

(d) processing the seed point to detect contour points of said tubular structure in the plane;

(e) analyzing the obtained contour points in the plane to predict a point along a tracing direction, such tracing direction being along a length of said tubular structure;

(f) establishing a new plane perpendicular to the tracing direction; and (g) repeating (c) through (f) until a predetermined criterion is satisfied.

* * * * *